US007582870B2

United States Patent
Lee et al.

(10) Patent No.: US 7,582,870 B2
(45) Date of Patent: Sep. 1, 2009

(54) IMAGING APPARATUS FOR IR FOUR-WAVE MIXING POLARIZATION MICROSCOPY

(75) Inventors: Jae Yong Lee, Chungbuk (KR); Eun Seong Lee, Daejeon (KR)

(73) Assignee: Korea Research Institute of Standards and Science, Daejeon (KR)

( * ) Notice: Subject to any disclaimer, the term of this patent is extended or adjusted under 35 U.S.C. 154(b) by 85 days.

(21) Appl. No.: 11/861,997

(22) Filed: Sep. 26, 2007

(65) Prior Publication Data
US 2008/0304047 A1 Dec. 11, 2008

(30) Foreign Application Priority Data
Jun. 8, 2007 (KR) ...................... 10-2007-0056085

(51) Int. Cl.
*G01J 3/00* (2006.01)
(52) U.S. Cl. .................................................. 250/338.1
(58) Field of Classification Search ............... 250/338.1; 356/301
See application file for complete search history.

(56) References Cited
U.S. PATENT DOCUMENTS 6,108,081 A * 8/2000 Holtom et al. .............. 356/301
6,798,507 B2 * 9/2004 Xie et al. .................... 356/301
2004/0057047 A1 * 3/2004 Knebel ....................... 356/301
2004/0145735 A1 * 7/2004 Silberberg et al. ........... 356/301
2005/0280827 A1 * 12/2005 Potma et al. ................ 356/485
2006/0238745 A1 * 10/2006 Hashimoto et al. ............ 356/73
2008/0059135 A1 * 3/2008 Murugkar et al. ............. 703/11
2008/0212166 A1 * 9/2008 Lett et al. .................... 359/326

* cited by examiner

*Primary Examiner*—David P Porta
*Assistant Examiner*—Marcus H Taningco
(74) *Attorney, Agent, or Firm*—The Webb Law Firm

(57) ABSTRACT

Disclosed is an imaging apparatus for IR four-wave mixing polarization microscopy. The apparatus can include pump and probe beam sources, a polarizer, a beam combiner, a scanner, an optical focusing system, a collecting optical system, a dichroic beam splitter, a polarizing beam splitter, a photodetector, a polarization differential detector, and a data analyzer. The technology can be used to obtain a molecular vibrational microscopic image using a polarization-dependent nonlinear spectroscopic signal obtained through the focusing and spatial scanning of multi-wavelength laser beams in a sample.

6 Claims, 5 Drawing Sheets

IMAGING APPARATUS FOR IR FOUR-WAVE MIXING POLARIZATION MICROSCOPY

TECHNICAL FIELD

The present invention relates to an IR four-wave mixing polarization microscope and a method thereof, more particularly, to a technology for obtaining a molecular vibrational microscopic image using a polarization-dependent nonlinear spectroscopic signal obtained by focusing and spatial scanning of multi-wavelength laser beams in a sample.

BACKGROUND ART

In observing an optically transparent micro-sample including a bio-sample like cells and tissues under a general optical microscope, there are some problems that it is very difficult to obtain a clear morphological image of various intracellular organs and materials in the sample and also it is impossible to selectively measure a spatial distribution of molecular chemical species. This is because a difference between objects and a background substance is minute in optical properties and thus a sufficient optical contrast therebetween is not provided. In other words, it is not easy to distinguish the specific microstructures or micro-materials to be observed from the background substance in the sample.

To explore phenomena of life science and disease mechanisms by observing behavior of intracellular organs or metabolites in cells through optical images, a laser scanning fluorescent microscope which could overcome a limitation of a general optical microscope has been widely used for a long time. According to an operation principle of the laser scanning fluorescent microscope, the sample is dyed with a fluorescent marker which selectively combines with the objects to be observed, and then fluorescence generated by scanning ultraviolet or visible laser irradiation is detected spatially, thereby obtaining an optical image in which the objects gain high contrast selectively. However, since the fluorescent marker as an exogenous material is added in the bio-sample, there is a basic problem that an original status of the bio-sample is not maintained as it was. Because the added exogenous material lowers activity of the bio-sample, it is difficult to obtain exact information about the behavior of the bio material. Furthermore, since a coloring matter of the fluorescent marker is easily photobleached even by very weak lasers, it is also difficult to observe the image continuously or in time-lapse measurements.

In order to avoid the disadvantages of the laser scanning fluorescent microscope, there has been proposed a new microscopic technology which can detect a spectroscopic characteristic of a material itself without the fluorescent marker which is selectively combined with molecules of the material and thus obtain a molecular image. As a representative method of analyzing spectroscopic signals of its own molecular vibrational fingerprint generated by interaction between particular molecules and laser beams, there are infrared absorption spectroscopy and Raman scattering spectroscopy which are combined with a microscopic optical system so as to be used for molecular image measurement of a microstructure.

FIG. 1 is a diagram of a molecular vibrational transition showing the principle of measuring an infrared absorption spectroscopic signal.

An infrared absorption microscope uses the principle that, when a laser beam scanned in a sample has a wavelength which resonates with inherent molecular vibration, the laser beam is strongly absorbed by the sample, and the intensity of the laser which is transmitted or reflected is reduced. The infrared absorption molecular image is obtained by measuring an attenuation ratio of the laser as a function of wavelength with respect to a scanning position of the laser beam.

FIG. 2 is a diagram of a molecular vibrational transition showing the principle of generating a spontaneous Raman spectroscopic signal.

In a Raman microscope, pixel data constructing a molecular image is formed by a spontaneous Raman spectrum generated by scanning the laser of a predetermined wavelength on the sample. Unlike in the infrared absorption microscope, a red-shifted Raman spectroscopic signal is generated by inelastic scattering of photons of the laser having a fixed wavelength which does not resonate with the molecular vibration of the objects. In this case, energy difference between incident photons and Raman-scattered photons corresponds to molecular vibration mode energy of materials in the sample. In other words, the Ramna spectrum obtained by collecting the laser beam scattered by the sample includes information about the inherent molecular vibration mode of the materials constituting the sample.

The infrared absorption microscope and the Raman microscope have various advantages and disadvantages, respectively.

Since the infrared absorption microscope is based on a linear absorption phenomenon, it is very simple to understand the principle and to analyze the signal. Furthermore, since the infrared absorption microscope uses a direct absorption spectroscopic signal generated from the resonance of the excitation laser and the molecular vibration mode, it offers high sensitivity and signal-to-noise ratio in the measurement. However, in the mid-IR regime with wavelength range of 2.5~18 µm where light is resonated with the molecular vibration and thus strongly absorbed, it is in practice very difficult to realize a wavelength-tunable laser beam source which is required for the microscopic image. Furthermore, due to the limitation imposed by diffraction phenomenon, the infrared absorption microscope has a very low spatial resolution of 10~40 µm compared with the spatial resolution (of 0.3~0.5 µm) in an optical microscope with a visible beam source. To solve the problem of lacking tunable mid-IR sources, a wavelength dispersive detector or an interferometer for fourier-transform spectroscopy is employed in the measuring part, in order for a white beam source having a wide spectrum from the visible to the mid-IR to be used.

On the contrary, since the Raman microscope uses a single wavelength beam source not related to a molecular vibrational frequency, the excitation laser is given less weight in constructing the Raman microscope, and its operation is very simple. Furthermore, since the Raman microscope uses a laser source having a short wavelength of the visible light range, it has an advantage of obtaining the microscopic image having a good spatial resolution. However, it has also a disadvantage that it takes a long time to obtain an image because the intensity of Raman signal for providing spectroscopic information is very weak. Particularly, in the case that a dynamic characteristic of the living bio-sample is observed, or an intensity of excitation laser cannot be sufficiently increased to avoid damage to the sample, the disadvantage becomes further serious.

Research and development has been carried out continuously to overcome the above disadvantages of the infrared absorption microscope and the Raman microscope.

In order to improve the low spatial resolution of the infrared absorption microscope, there has been proposed a scanning near-field IR microscope using metal-coated optical fiber in which an aperture of a few hundred nm is formed at a distal end of a tip. Herein, the spatial resolution does not depend on the IR diffraction limitation, but depends on the size of aperture formed at the tip of the optical fiber, regardless of the wavelength of a laser beam, thereby providing the spatial resolution comparable with that in the optical microscope using a visible beam source. However, in order to obtain the microscopic image, it is necessary for a surface of the sample to be mechanically scanned with high precision relative to the tips of the optical fiber, but it is difficult to quickly obtain the image since the aperture has a very low transmission efficiency ($\sim 10^{-6}$) at IR wavelengths. In addition, with a current technical standard, it is difficult to provide a reliable process technology which manufactures the optical fiber for efficiently transferring the IR. That is, it overcomes the limitation of the spatial resolution, whereas it submits to a sacrifice of the measurement sensitivity and the speed for obtaining the microscopic image.

A coherent andti-Stokes Raman scattering (CARS) microscope overcomes substantially low sensitivity and slow speed for obtaining the microscopic image which were critical disadvantages in the conventional Raman microscope. In detecting of molecular vibrations, CARS is also based on the Raman scattering phenomenon is similar to that in the conventional Raman microscope. However, the fundamental difference is not to use the spontaneous Raman scattering as a linear optical phenomenon, but to use a four wave mixing in which three incident laser beams are interacting with the sample so as to generate a nonlinear optical signal.

FIG. 3 is a diagram of a molecular vibrational shift showing a principle of generating a CARS nonlinear spectroscopic signal.

Referring to FIG. 3, two incident laser beams (pump beam and Stokes beam) having a frequency difference corresponding to Raman shift of a certain molecule in the sample generate a beat and then induces forced harmonic molecular vibration which is coherent with the beat waveform. If a third laser beam (probe beam) is incident on the molecules which are vibrating in phase with coherence a status that phases are harmonized, anti-Stokes Raman scattering whose wavelength becomes shorter takes place through interaction, resulting in a coherent signal beam having the same phase in a predetermined propagating direction. Then, the nonlinear optical signal is precisely mapped in a space of the sample, thereby obtaining the CARS microscopic image.

The CARS microscope has an advantage of providing a very high measurement sensitivity and high speed for obtaining the image as well as obtaining the selective image. Since the CARS generates a very intense signal beam than the spontaneous Raman scattering, it is possible to quickly obtain high quality images having a good signal-to-noise ratio. The CARS phenomenon depends on the characteristic of third-order nonlinear optical susceptibility inherent to a material that give rise to four wave mixing, and therefore provides a signal enhancement proportional to the cube of incident laser beam intensity, and also provides a mechanism of obtaining a three-dimensional image of an inner portion of the sample with a high spatial resolution, as in laser confocal microscopes. Moreover, since the CARS phenomenon is an optical parametric conversion process which does not dissipate any laser energy in the measured sample after the interaction, it is a non-invasive measuring method which can avoid thermal damage to the sample by the laser.

However, the CARS microscope has also some disadvantages that the molecular selectivity and the signal-to-noise ratio are lowered by the non-resonant third-order nonlinear optical susceptibility which is not relevant to the natural vibration of molecules, and the measurement sensitivity is still low in comparison with a method using direct resonance absorption in the mid-IR range.

DISCLOSURE OF THE INVENTION

It is an object of the present invention to provide an imaging apparatus for IR four-wave mixing polarization microscopy, which uses molecular vibrational resonance of IR laser and overcomes the problem that the spatial resolution is seriously lowered by the diffraction limit, when detecting an inherent molecular vibration of materials in a sample without staining the sample or adding fluorescent markers.

It is another object of the present invention to provide an imaging apparatus for IR four-wave mixing polarization microscopy, which employs a far-field optical method which facilitates implementations in a diversity of application fields, instead of an access method using a near-field optical probe which is applied in the prior art, so as to secure the spatial resolution.

It is yet another object of the present invention to provide a new nonlinear optical four wave mixing polarization spectroscopy as a core principle which can take advantage of measurement sensitivity caused by using the mid-IR laser beam source and also overcome a disadvantage in an aspect of spatial resolution.

It is yet another object of the present invention to provide a nonlinear signal collecting and processing optical system which can be practically realized in a microscopic imaging system.

Hereinafter, the present invention is described in detail.

To achieve the objects of the present invention, there has been provided an imaging apparatus for IR four-wave mixing polarization microscopy, comprising a pump beam source 10 for generating an infrared pump beam which excites medium molecules constituting a sample with a frequency in the molecular vibration band so as to be resonated with each other and thus forms a coherence status; a probe beam source 20 for generating a probe beam which detects the molecular coherence status locally induced in a sample by the infrared pump beam; a polarizer 11, 21 for linearly polarizing the pump beam and probe beam; a beam combiner 30 which synchronizes temporally and overlaps spatially the polarized pump beam and probe beam on the same path; a scanner 40 for two-dimensionally scanning the pump beam and the probe beam that are combined by the beam combiner 30 so as to obtain a microscopic image; an optical focusing system 50 for focusing the scanned pump beam and probe beam on a local point within the sample; a collecting optical system 60 for collecting the signal light which is generated by the input beams focused by the optical focusing system 50 to interact with the sample and of which phase is anisotropically retarded by nonlinear birefringence of the sample, and then collimating the signal light into a parallel beam; a dichroic beam splitter 70 for removing the infrared pump beam out of the parallel beam formed by the collecting optical system 60 and splitting only the signal beam; a polarizing beam splitter 80 for converting the signal beam split out by the dichroic beam splitter 70 into linearly polarized beams having their polarization axes perpendicular to each other; a photodetector 91, 92 for detecting an intensity of each of the linerly polarized beams converted by the polarizing beam splitter 80; a polarization differential detector 100 for detecting a polarization difference based on the intensities of the linerly polarized beams detected by the photodetector 91, 92, and a data analyzer 110 for acquiring the polarization difference detected by the polarization differential detector 100 and generating and extracting a spectrospcopic signal depending on a molecular vibrational strength of the sample.

Preferably, the polarization differential detector 100 produces an amplified polarization differential signal by subtracting a left circular polarization component from a right circular polarization component that are transformed and split into two linearly polarized beams.

Preferably, the the photodetector 100 uses a lock-in amplifier 111 in which a second harmonic of the modulation frequency of the polarization differential signal is set as a reference frequency.

Preferably, the pump beam source is a wavelength-tunable beam source affording molecular vibrational resonance, realized through a DFG method (difference frequency generation) using a wavelength-tunable visible/near-infrared pulsed laser and a wavelength-fixed pulsed laser.

Preferably, the scanner 40 uses a galvano-mirror so as to scan the beam combined with the pump beam and probe beam at high speed on a two-dimensional plane.

Preferably, the photodetector 91, 92 is a photomultiplier tube for detecting the optical signal with high amplification, or a high speed photodiode.

Further, the imaging apparatus of the present invention is used as a microscopic imaging apparatus.

DETAILED DESCRIPTION OF MAIN ELEMENTS

Figure 1:
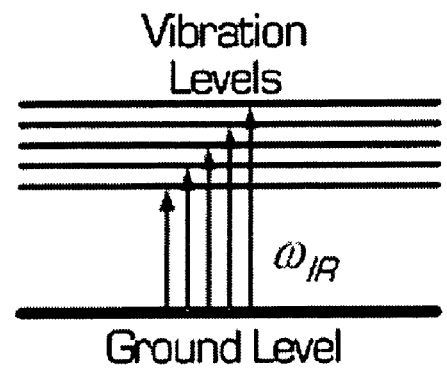
FIG. 1 is a diagram of a molecular vibrational transition showing a principle of measuring an infrared absorption spectroscopic signal.
Figure 2:
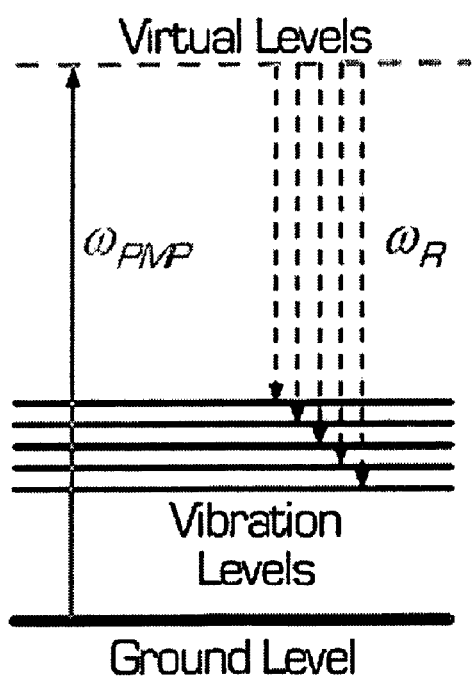
FIG. 2 is a diagram of a molecular vibrational transition showing a principle of generating a spontaneous Raman spectroscopic signal.

10: pump beam source
11, 21: polarizer
40: scanner
50: optical focusing system
60: collecting optical system
70: dichroic beam splitter
80: polarizing beam splitter
91, 92: photodetector
100: polarization differential detector
110: data analyzer 20: probe beam source
30: beam combiner

Best Mode for Carrying Out the Invention

Practical and presently preferred embodiments of the present invention are illustrated as shown in the following Examples and Comparative Examples.

However, it will be appreciated that those skilled in the art, on consideration of this disclosure, may make modifications and improvements within the spirit and scope of the present invention.

Figure 4:
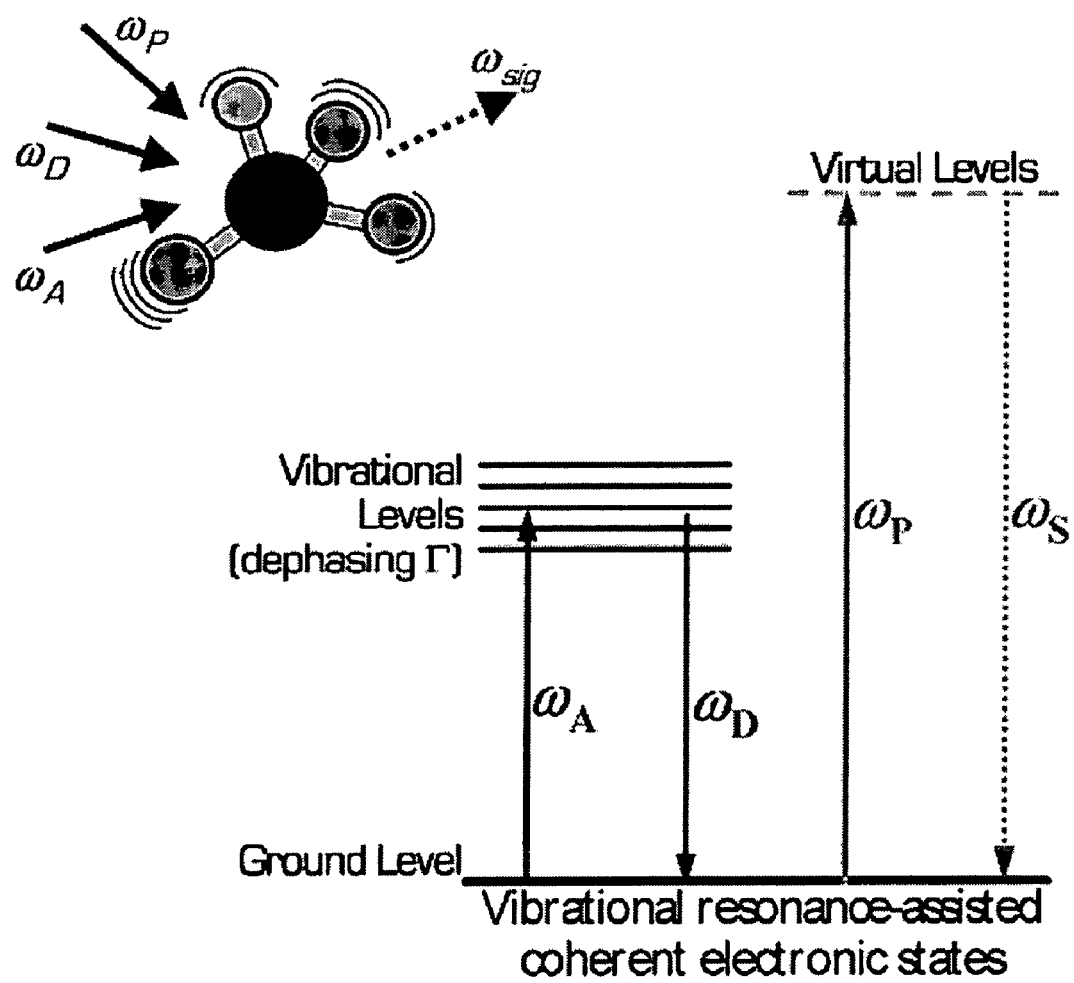
FIG. 4 is a diagram of laser-sample interaction energy level and transition which are proposed by an IR four-wave mixing polarization differential detection according to the present invention.

FIG. 4 is a diagram of laser-sample interaction energy level and transition which are proposed by an IR four-wave mixing polarization differential detection according the present invention.

In obtaining a selective spectroscopic signal with respect to a certain molecular vibration, if a laser having a frequency $\omega_A$ which resonates with the molecular vibration is incident to a sample, the laser is strongly absorbed. In this case, if a peak power of the laser is high enough, the molecule excited to a molecular vibrational energy level is resonantly de-excited back to a ground energy level. In this case, a frequency $\omega_D$ of the laser is the same as the absorbed frequency $\omega_A$, and thus the resonance absorption and the de-excitation to the ground level are occurred by that the substantially same laser provides coherence so as to cause the two actions in sequence. The sample returns to the ground energy level by the interaction with the laser, but an internal status of the sample is changed by the resonance transitions so as to have electronic coherence, which is different from its original status.

In a molecular aggregate having electronic coherence, a nonlinear refractive index change $\Delta n = n_2 I_{IR}$ proportional to an intensity of laser beam $I_{IR}$ and a material coefficient $n_2$ is induced additively to its original refractive index $n_0$. The material coefficient $n_2$ depends on a concentration of a particular molecule in the sample, and a degree of resonance depends on a wavelength or frequency of the infrared pump beam. In the case that the infrared pump beam is in a particular linear polarization state, the nonlinear refractive index which is induced to the material through the molecular vibrational resonance becomes anisotropic. That is, since a nonlinear refractive index $\Delta n_\parallel$ in a direction parallel with a polarization axis of the infrared pump beam and a nonlinear refractive index $\Delta n_\perp$ in a direction perpendicular to the polarization axis of the infrared pump beam have a different value, a nonlinear birefringence phenomenon of $(\Delta n_\parallel - \Delta n_\perp)$ is occurred. At this time, if a probe beam having a nonresonant frequency $\omega_P$ is incident to the sample, a signal, which has the same frequency $\omega_S$ as that of the probe beam and in which its phase is changed, is generated according to the nonlinear refractive index change.

Figure 5:
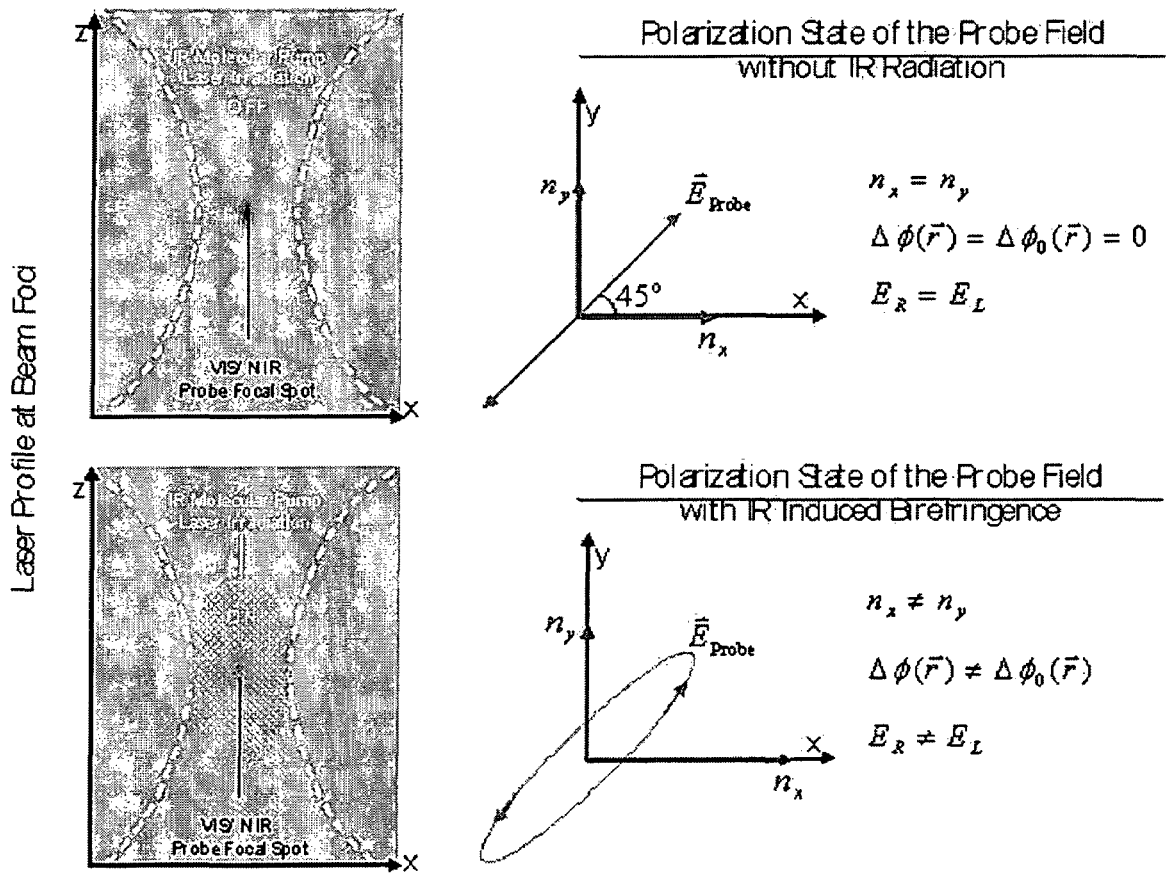
FIG. 5 is a schematic view showing polarization states of laser beams and spatial resolution features used for signal beam analysis in an IR four-wave mixing polarization imaging method according to the present invention.

FIG. 5 is a schematic view showing polarization states and spatial resolution characteristic used for signal beam analysis in an IR four-wave mixing polarization imaging method according to the present invention.

As described above, the spectroscopic signal of the present invention is generated when the beam ($\omega_A$, $\omega_D$) for is inducing the resonance absorption in the infrared and the de-excitation back to the ground level is spatially coincident with the probe beam ($\omega_P$) of visible/near-infrared band for detecting the nonlinear birefringence. Each laser beam, which is used to generate the spectroscopic signal having a good spatial resolution in a microscope, needs to be focused by objective lens and also localized at the same time.

In the case that there is no infrared pump beam ($\omega_A$, $\omega_D$) present, the probe beam of the visible/near-infrared band ($\omega_P$) is focused in the sample and then output as the signal beam having the initial frequency ($\omega_S = \omega_P$), which does not include any information of the molecular vibration. However, if the infrared laser beam ($\omega_A$, $\omega_D$) is interacted with the molecular vibration of the sample, a signal beam, which has the same frequency ($\omega_S=\omega_P$) but with anisotropic phase retardation $\Delta\Phi$ resulting from the birefringence, can be obtained from the probe beam ($\omega_P$) focused in the sample. In other words, by measuring a magnitude of the anisotropic phase retardation $\Delta\Phi$ of the signal beam between the case that the infrared laser beam ($\omega_A$, $\omega_D$) exists and the case that the infrared laser beam ($\omega_A$, $\omega_D$) does not exist, a concentration of chemical species whose molecular resonance resides distinctively at a specific frequency ($\omega_A=\omega_D$), can be quantified.

In order to facilely measure a modulation amplitude of the anisotropic phase delay $\Delta\Phi$, the present invention proposes a method of detecting intensity difference between orthogonal polarization components of a signal beam in which polarization distortion increases with the anisotropic phase delay $\Delta\Phi$.

Figure 3:
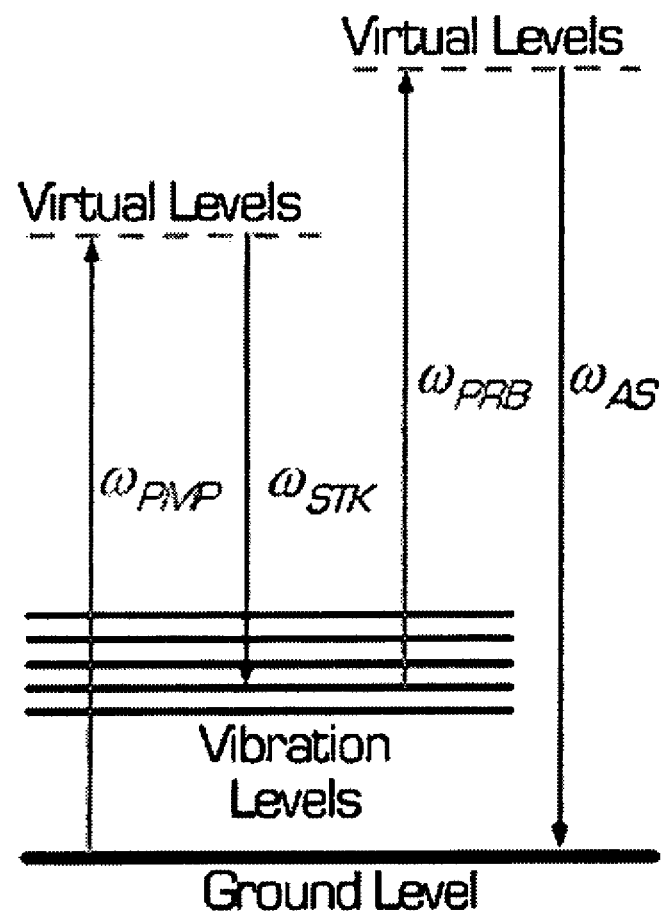
FIG. 3 is a diagram of a molecular vibrational transition showing a principle of generating a CARS nonlinear spectroscopic signal.

As shown in FIG. 3, if the infrared pump beam is not incident, the nonlinear birefringence phenomenon of ($\Delta n_\parallel - \Delta n_\perp$) is not occurred. Therefore, the sample keeps its original refractive index distribution $n_x=n_y$, and also there is no anisotropic phase retardation $\Delta\Phi$. Therefore, if a linearly polarized probe beam passes through the sample, the polarization state remains unchanged. However, if an infrared pump beam, which is linearly polarized in either x- or y-axial direction, passes through the sample, the infrared pump beam makes resonance with sample and thus the refractive index ($n_x \neq n_y$) in the in x- or y-axial direction is changed by the nonlinear birefringence. When the anisotropic phase delay $\Delta\Phi$ is induced, the probe beam, which is linearly polarized at an angle of 45 degrees with respect to the x-axis, changes into an elliptical polarization state depending on the magnitude of the anisotropic phase retardation $\Delta\Phi$, after passing through the sample.

An arbitrary linear polarization vector in $\vec{E}_{lin}$ is expressed by superposition of right circular polarization $\vec{E}_R$ and left circular polarization $\vec{E}_L$, and this is the case that the two circular polarization vectors have the same magnitude ($|\vec{E}_R|=|\vec{E}_L|$). An elliptical distortion of the polarization state caused by the birefringence ($\Delta n_\parallel - \Delta n_\perp$) or anisotropic phase retardation $\Delta\Phi$ of the sample, is quantified by how much the right circular polarization component and left circular polarization component are not balanced in the magnitude. ($|\vec{E}_R|-|\vec{E}_L|\neq 0$). In quantifying the interaction between the infrared pump beam and the sample, the present invention is characterized by letting a linearly polarized probe beam $\vec{E}_{lin}$ pass through the sample, and then measuring the difference between $|\vec{E}_R|^2$ and $|\vec{E}_L|^2$, the light intensities in the right circular polarization and left circular polarization, respectively, of the polarization distorted beam. The characteristic provides an advantage which can measure the anisotropic phase retardation $\Delta\Phi$ without an interferometer which is usually complicated and troublesome to use.

Further, the spatial resolution of the nonlinear spectroscopic imaging apparatus according to the present invention has a different characteristic from other imaging apparatus used in a general laser microscope.

The theoretical limit of spatial resolution in a general optical image which is obtained by using the laser beam focused through an objective lens of a microscope is $\delta R=\lambda/2NA$ in the lateral direction (x-axis or y-axis), and $\delta Z \approx 3\lambda r$ in the longitudinal direction (z axis). Herein, the "$\lambda$" is a wavelength of the focused laser beam, and the "NA" is a numerical aperture of the objective lens which is determined by a refractive index of a medium and a focusing angle of the beam. A minimum focal spot size with infrared laser beams for inducing the resonance absorption and de-excitation, is limited to 2.5~18 µm, and the spatial resolution of the infrared microscope depends on this limit.

However, the present invention is characterized in that the spatial resolution is improved by using the inherent nonlinear optical phenomenon in which a plurality of laser beams having different wavelengths are made to interact with the sample. The nonlinear spectroscopic signal according to the present invention is generated from the light wave $E\omega_S$ of the frequency $\omega_S$ which is re-radiated by a third-order nonlinear polarization $P\omega_S^{(3)}=\chi^{(3)}E\omega_A E\omega_D^* E\omega_P$ of the sample. That is, the observation can be achieved only when the light waves $E\omega_A$, $E\omega_D$, and $E\omega_P$ having frequencies $\omega_A$, $\omega_D$, and $\omega_P$, respectively, are synchronously positioned at the same place within the sample having a third-order nonlinear susceptibility $\chi^{(3)}(\omega_S;\omega_A,-\omega_D,\omega_P)$. In the case that each of the incident light waves is focused into a finite volume by the objective lens, the generation of signal beam is localized to a spot in which all of the light waves are overlapped spatially and the product of amplitudes becomes non-zero.

According to the present invention, the diffraction limit of the laser beam for inducing the resonance absorption ($E\omega_A$) and de-excitation ($E\omega_D$) of the infrared band is 2.5 ~18 µm, but a final spatial resolution of 0.3~0.7 µm is obtained by the probe beam ($E\omega_P$) of the visible/near-infrared band which can be tightly focused to a much smaller focal volume.

Figure 6:
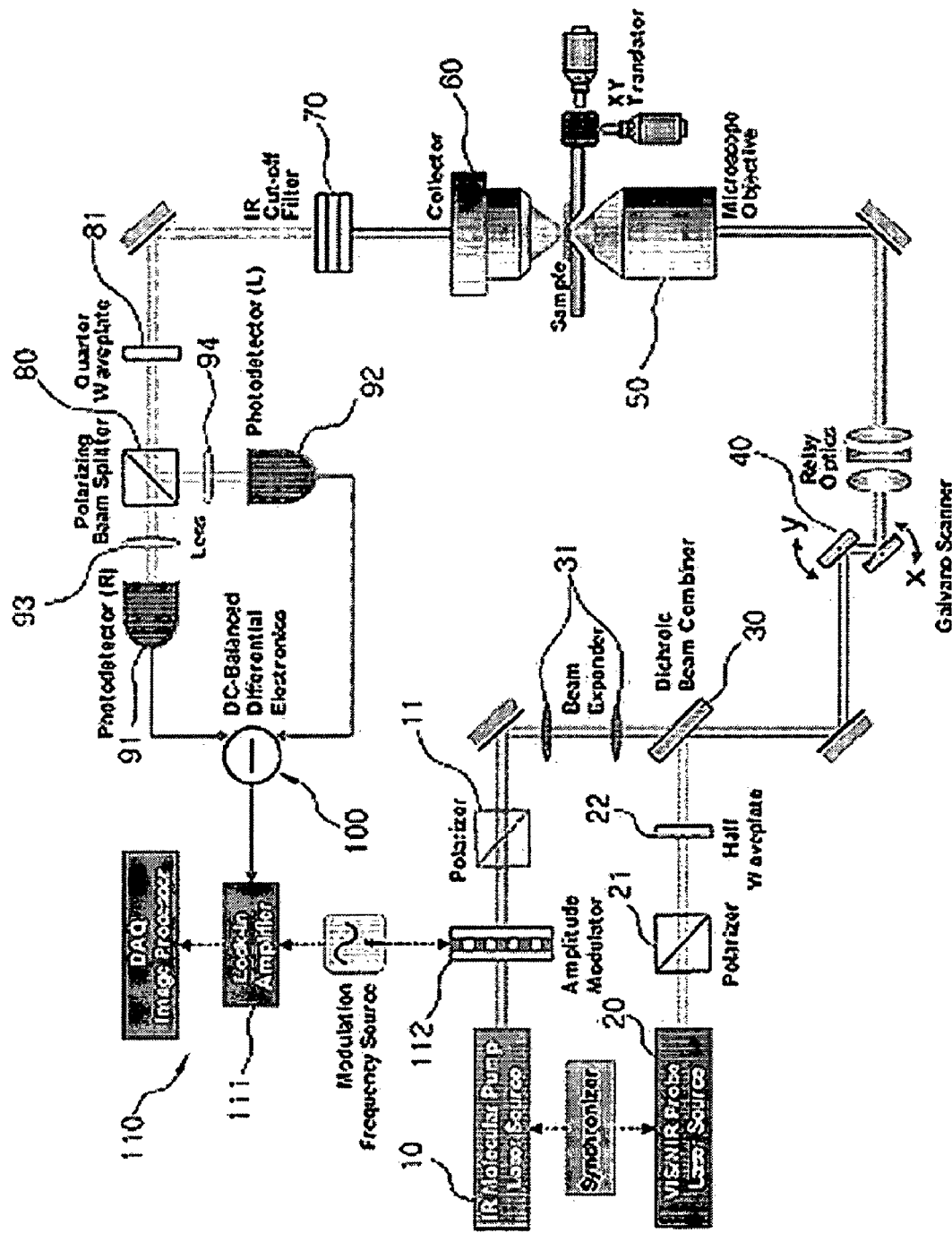
FIG. 6 is a view showing a construction of a microscopic imaging apparatus using the IR four-wave mixing polarization differential detection according to the present invention.

FIG. 6 is a view showing a construction of a microscopic imaging apparatus using the IR four-wave mixing polarization differential detection according to the present invention. The microscopic imaging apparatus is an example using a polarimetric device which measures the phase change of the nonlinear optical signal and extracts the molecular vibrational spectroscopic signal.

As shown in drawing, an imaging apparatus for IR four-wave mixing polarization microscopy according to the present invention includes a pump beam source 10 for generating an infrared pump beam; a probe beam source 20 for generating a probe beam; a polarizer 11, 21 for linearly polarizing the pump beam and probe beam; a beam combiner 30 which synchronizes temporally and overlaps spatially the polarized pump beam and probe beam on the same axis; a scanner 40 for two-dimensionally scanning the combined pump beam and probe beam; an optical focusing system 50 for focusing the scanned pump beam and probe beam on a local point within the sample; a collecting optical system 60 for collecting the beam which is generated by the focused beams interacting with the sample to yield anisotropic phase retardation by nonlinear birefringence of the sample and then forming a parallel beam; a dichroic beam splitter 70 for removing the infrared pump beam out of the parallel beam and splitting out only the probe beam whose phase is anisotropically retarded; a polarizing beam splitter 80 for converting the filtered probe beam into linearly polarized beams having their axes perpendicular to each other; a photodetector 91, 92 for detecting an intensity of each of the converted linerly polarized beams; a polarization differential detector 100 for detecting a polarization difference based on the detected intensities of the linerly polarized beams; and a data analyzer 110 for acquiring the detected polarization difference signals and extracting a spectrospcopic information corresponding to the strength of molecular vibrational coherence of the sample.

The infrared pump beam source 10 functions to generate the infrared pump beam which excites medium molecules constituting the sample at a frequency of certain molecular vibration band so as to be resonated with each other and thus forms a coherence state. The pump beam source 10 is a wavelength-tunable light source for providing two light wave components which cause an absorption (frequency $\omega_A$) resonated with the molecular vibration, and a ground level de-excitation (frequency $\omega_P$). Preferably, the pump beam source 10 outputs a repetitive pulse having a high peak power.

The probe beam source 20 functions to generate the probe beam for detecting the coherence state which is locally induced in the sample by the infrared pump beam. The probe beam source 20 generates the probe beam having a frequency ($\omega_P$) in a visible or IR band, and also generates a signal beam (frequency $\omega_S = \omega_P$) while passing through a molecular aggregate with molecular coherence.

At this time, the infrared pump beam source 10 and visible pump beam source 20 use a synchronizer for performing pulse timing synchronization with high precision and an optical pulse delay generator, so as to output a temporally overlapped ultrashort pulse train.

The infrared pump beam and visible pump beam which are synchronized temporally are passed through a polarization regulation unit 25 including a waveplate 22 and the polarizer 11, 21 for linearly polarizing the pump beam and probe beam, and then converted into an input polarization states which is needed by the method of detecting IR four-wave mixing polarization difference. At this time, a linear polarizer is used as the polarizer 11, 21. The infrared pump beam is passed through the polarizer 11 so as to be a linear polarization state having a high extinction ratio, and it will be regarded as an x-axial linear polarization state. The visible probe beam is also passed through the other polarizer 21 and thus converted into the linear polarization status, however, it is aligned at an inclination of 45 degrees with respect to the x-axis by passing through a half waveplate 22.

The infrared pump beam and visible pump beam, whose polarization states are set, are spatially overlapped on the same axis and then combined by an additional device for matching their beam sizes. The additional device includes a beam expander 31 which is positioned either in a pump or in a probe beam path, and a beam combiner 30 for synchronizing and overlapping the pump beam and probe beam temporally and spatially on the same axis.

The beam combiner 30 is a dichroic beam combiner in which the pump beam and the probe beam in different frequency bands have opposite characteristics in reflection and transmission.

The pump beam and probe beam combined by the beam combiner 30 are two-dimensionally scanned by the scanner 40 so as to obtain a microscopic image, and directed to a microscope objective lens, i.e., the optical focusing system 50 which is positioned at the front side of the sample, and focused on a local point within the sample. And the focused probe beam is interacted with the sample and then anisotropically delayed by the linear birefringence.

The collecting optical system 60 collects the signal beam which is generated by the focused beams interacting with the sample to induce the anisotropic phase retardation by the nonlinear birefringence of the sample, and forms a parallel beam.

After the beam is collimated into the parallel beam by the collecting optical system 60, the beam passes through the dichroic beam splitter 70 as an IR cut-off filter for removing the infrared pump beam. Therefore, only the probe beam, of which the phase is anisotropically delayed by the nonlinear birefringence, is splitted.

The dichroic beam splitter 70 functions to remove the infrared pump beam out of the parallel beam collimated by the collecting optical system 60 and the split the probe beam of which the phase is anisotropically delayed. The filtered probe beam of which the phase is anisotropically delayed is converted into the linerly polarized beams by the polarizing beam splitter 80.

The polarizing beam splitter 80 functions to convert the splitted and anisotropically phase-retarded probe beam into two linearly polarized beams having the axial components perpendicular to each other. The intensity of each of the linerly polarized beams converted by the polarizing beam splitter 80 is detected by the photodetector 91, 92. On the basis of the detected intensities of the linerly polarized beams, the polarization difference is detected by the polarization differential detector 100. The detected polarization difference is collected by the data analyzer 110 and then generates and extracts the spectrospcopic signal according to the molecular vibrational coherence strength of the sample.

A polarization-split signal beam generator for measuring the polarization distortion by the molecular vibrational coherence of the sample includes a quarter waveplate 81 and the polarizaing beam splitter 80. The quarter waveplate 81 functions to convert a right circularly polarized beam wave $\vec{E}_R$ contained in the probe beam into a linearly polarized beam along x-axis and also convert a left circularly polarized beam wave $\vec{E}_L$ into a linearly polarized beam along y-axis, when a fast axis is aligned at an angle of $-45$ degrees with respect to the x-axis. Further, the polarizaing beam splitter 80 may be aligned so as to transmit the linearly polarized beam $\vec{E}_x$ along x-axis but reflect the linearly polarized beam $\vec{E}_y$ along y-axis. Therefore, the combination of the quarter waveplate 81 and the polarizaing beam splitter 80 functions to split the right circularly polarized beam wave component and the left circularly polarized beam wave component contained in the probe beam so as to output a polarization signal beam to a transmitting end and a reflecting end, respectively.

If a focusing lens 93, 94 and the photodetector 91, 92 are disposed respectively at the transmitting end and the reflecting end of the polarization splitted signal beam generator, $I_R = |\vec{E}_R|^2$ and $I_L = |\vec{E}_L|^2$, the intensities of the right circularly polarized beam and left circularly polarized beam, respectively, contained in the signal beam can be measured.

The polarization differential detector 100 for the polarization-split signal beam includes the photodetector 91 for measuring an intensity $I_R$ of the right circularly polarized signal beam and then converting it into an electric signal, the photodetector 92 for measuring an intensity $I_L$ of the left circularly polarized signal beam and then converting it into an electric signal, and a differential amplifier 111 for producing a signal proportional to a difference $I_R - I_L$ between signals of the two photodetectors 91 and 92. Herein, the two photodetectors 91 and 92 have the same performance and characteristic.

Assuming that an amount of the anisotropic phase retardation by the nonlinear birefringence ($n_x \neq n_y$) of the sample is $\Delta\Phi$, a signal obtained by the polarization differential detector is expressed as follows:

$$I_R - I_L = 4I_O \Delta\Phi(\vec{r}; t)$$

Herein, the $I_O$ is the sum $I_R + I_L$ of the polarization-split signal beams. The amount $\Delta\Phi$ of the anisotropic phase retardation is generally changed with the state of the sample as a function of spatial position ($\vec{r}$) and time (t) of the heterogeneous sample.

Preferably, the polarization differential detector 100 of the present invention uses an additional unit for temporally modulating the nonlinear birefringence ($\Delta n_\parallel - \Delta n_\perp$) due to the molecular vibrational resonance of the sample and measuring a polarization differential detecting signal. The additional unit modulates the field amplitude ($E_{IR}$) of the infrared pump beam at angular frequency ($\omega_m$) by using an amplitude modulator 112 which is positioned at the front side of the infrared pump beam source, and then measures the resulting modulation amplitude of the polarization differential signal due to the anisotropic phase retardation $\Delta\Phi$ corresponding to the modulation by using a lock-in amplifier 111.

The intensity $I_{IR}$ of the infrared pump beam which induces the nonlinear birefringence of the sample is modulated as follows:

$$I_B = I_{IR}\cos^2\omega_m t = I_{IR}\left[\frac{1+\cos 2\omega_m t}{2}\right]$$

Therefore, assuming that the anisotropic phase retardation $\Delta\Phi$ of the sample is proportional to an intensity $I_B$ of the modulated infrared pump beam and an coefficient $d(\vec{r})$ according to a spatial characteristic of the nonuniform sample, an amount of the anisotropic phase delay can be expressed as follows:

$$\Delta\phi(\vec{r};t) = d(\vec{r})\cdot I_{IR}\left[\frac{1+\cos 2\omega_m t}{2}\right] + \Delta\phi_0(\vec{r})$$

At this time, the $\Delta\phi_0(\vec{r})$ means a phase retardation term due to the birefringence of the sample irrelevant to the infrared pump beam modulation, and it can be generally neglected. The anisotropic phase retardation $\Delta\phi(\vec{r};t)$ can be divided into an AC component $\Delta\phi_{AC}(\vec{r})$ and a DC component $\Delta\phi_{DC}(\vec{r})$ and each of the components is as follows:

$$\Delta\phi_{AC}(\vec{r}) = \frac{d(\vec{r})\cdot I_{IR}}{2}$$

$$\Delta\phi_{DC}(\vec{r}) = \frac{d(\vec{r})\cdot I_{IR}}{2} + \Delta\phi_0(\vec{r})$$

If the lock-in amplifier 111 is operated with a reference set to the second harmonic of an amplitude modulation frequency $f=\omega_m/2\pi$ of the pump beam, a contribution term $\Delta\phi_{DC}(\vec{r})$ of the anisotropic phase retardation without temporal modulation is removed. Finally, a normalized polarization differential modulation amplitude as a molecular vibrational detection signal of the sample is obtained as follows:

$$\frac{I_m(2\omega_m)}{I_0} = 4\Delta\phi_{AC}(\vec{r})$$

The IR four-wave mixing polarization is obtained by measuring the molecular vibrational detection signal according to the spatial position $\vec{r}$. To this end, the scanner 40 is used to sweep the focal position of the laser beam three dimensionally in the sample.

Preferably, the scanner 40 of the present invention uses a motorized scanner which mechanically translates the position of the sample relative to a fixed laser focus on the xy-plane and in the z-axial direction, or deflects the beam combined with the pump beam and probe beam at a high speed on a two dimensional plane by a galvano mirror.

Preferably, the imaging apparatus for infrared nonlinear molecular vibrational microscopy according to the present invention is used in a high resolution microscope.

According to the present invention, since a nonlinear optical four-wave mixing spectroscopy is employed in the infrared molecular vibrational imaging system, it is possible to provide a far-field laser microscope with excellent detection sensitivity and spatial resolution.

INDUSTRIAL APPLICABILITY

According to the present invention, as described above, by using the infrared pump beam which is strongly resonated with the molecular vibration, it is possible to solve the problem of low detection sensitivity in the conventional molecular vibrational microscope based on spontaneous Raman scattering and coherent anti-Stokes Raman scattering (CARS). Furthermore, by extracting the nonlinear molecular vibration spectroscopic signal through the probe beam having a short wavelength, it is possible to solve the problem of unsatisfactory spatial resolution of the conventional linear IR absorption molecular vibrational microscope, there obtaining an excellent resolution. Furthermore, the present invention can contribute to remarkably improve the image acquisition speed and the image quality in the field of molecular vibrational microscope.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. An imaging apparatus for JR four-wave mixing polarization microscopy, comprising:
   a pump beam source for generating an infrared pump beam which excites medium molecules constituting a sample with a frequency in molecular vibration bands so as to be resonated with each other and thus forms a molecular vibration coherence;
   a probe beam source for generating a probe beam which detects the molecular coherence of a sample locally induced by the infrared pump beam;
   a polarizer for linearly polarizing the pump beam and the probe beam;
   a beam combiner which synchronizes temporally and overlaps spatially the polarized pump beam and probe beam on the same path;
   a scanner for two-dimensionally scanning the pump beam and the probe beam combined by the beam combiner so as to obtain a microscopic image;
   an optical focusing system for focusing the scanned pump beam and probe beam on a local point within the sample;
   a collecting optical system for collecting the beam which is formed by that the beams focused by the optical focusing system are interacted with the sample and of which phase is anisotropically retarded by nonlinear birefringence of the sample, and then forming a parallel beam;

a dichroic beam splitter for removing the infrared pump beam out of the parallel beam formed by the collecting optical system and splitting the probe beam of which phase is anisotropically retarded;

a polarizing beam splitter for converting the probe beam splitted and anisotropically phase-retarded by the dichroic beam splitter into linerly polarized beams having axial components perpendicular to each other;

a photodetector for detecting an intensity of each of the linearly polarized beams converted by the polarizing beam splitter;

a polarization differential detector for detecting a polarization difference based on the intensities of the linerly polarized beams detected by the photodetector; and a data analyzer for collecting the polarization difference detected by the polarization differential detector and generating and extracting a spectrospcopic signal according to a molecular vibrational coherence strength of the sample.

2. The imaging apparatus as set forth in claim 1, wherein the polarization differential detector amplifies a polarization differential signal detected by splitting a right circular polarization component and a left circular polarization component of each of the detected linearly polarized beams.

3. The imaging apparatus as set forth in claim 2, wherein the polarization differential detector uses a lock-in amplifier in which the second harmonic of the modulation frequency of the polarization differential signal is set as a reference frequency.

4. The imaging apparatus as set forth in claim 1, wherein the pump beam source is a wavelength-tunable beam source affording molecular vibrational resonance, realized by a DFG method (difference frequency generation) using a wavelength-tunable visible/near-infrared pulsed laser and a wavelength-fixed pulsed laser.

5. The imaging apparatus as set forth in claim 1 wherein the scanner uses a galvano-minor so as to scan the beam combined with the pump beam and probe beam at high speed on a two-dimensional plane.

6. The imaging apparatus as set forth in claim 1, wherein the photodetector is a photomultiplier tube for detecting the optical signal with high amplification, or a high speed photodiode.

* * * * *

UNITED STATES PATENT AND TRADEMARK OFFICE
CERTIFICATE OF CORRECTION

| | | |
|---|---|---|
| PATENT NO. | : 7,582,870 B2 | Page 1 of 1 |
| APPLICATION NO. | : 11/861997 | |
| DATED | : September 1, 2009 | |
| INVENTOR(S) | : Lee et al. | |

It is certified that error appears in the above-identified patent and that said Letters Patent is hereby corrected as shown below:

Column 12, Line 43, Claim 1, "apparatus for JR" should read --apparatus for IR--

Column 13, Line 7, Claim 1, "linerly" should read --linearly--

Column 13, Line 13, Claim 1, "linerly" should read --linearly--

Column 14, Line 15, Claim 5, "galvano-minor" should read --galvano-mirror--

Signed and Sealed this

Nineteenth Day of January, 2010

David J. Kappos
*Director of the United States Patent and Trademark Office*